United States Patent
Becker

[19]

[11] Patent Number: 6,113,569
[45] Date of Patent: Sep. 5, 2000

[54] RECIPROCATING LIPOSUCTION DEVICE

[75] Inventor: Hilton Becker, Boca Raton, Fla.

[73] Assignee: Very Inventive Physicians, Tucson, Ariz.

[21] Appl. No.: 08/576,632

[22] Filed: Dec. 21, 1995

[51] Int. Cl.[7] .................................................. A61M 1/00
[52] U.S. Cl. ........................... 604/35; 604/121; 604/542
[58] Field of Search .................................. 604/22, 27, 31,
604/35, 43, 65, 95, 102, 119, 121, 156–157,
158–165, 174, 152, 902, 141, 542, 40;
606/107, 171

[56] References Cited

U.S. PATENT DOCUMENTS

| | | |
|---|---|---|
| 4,909,249 | 3/1990 | Akkas . |
| 4,940,468 | 7/1990 | Petillo . |
| 4,985,027 | 1/1991 | Dressel . |
| 4,986,827 | 1/1991 | Akkas et al. . |
| 5,102,410 | 4/1992 | Dressel . |
| 5,275,607 | 1/1994 | Lo et al. . |
| 5,352,194 | 10/1994 | Greco et al. . |

*Primary Examiner*—Wynn Wood Coggins
*Assistant Examiner*—A. T. Nguyen
*Attorney, Agent, or Firm*—Mark E. Ogram P.C.

[57] ABSTRACT

Apparatus is disclosed for performing liposuction in which the reciprocal motion of the cannula during the operation is automated. The apparatus includes a housing, a cannula and reciprocating arrangement to provide the motion for the cannula. In one arrangement, the suction being applied to the cannula to remove fatty tissue has the negative pressure created by the suction applied to the cannula to reciprocate it. In a second embodiment, a permanent magnet piston attached to the cannula is reciprocated by the use of electromagnets which simultaneously change polarity to apply a reciprocating force to the permanent magnet piston.

12 Claims, 4 Drawing Sheets

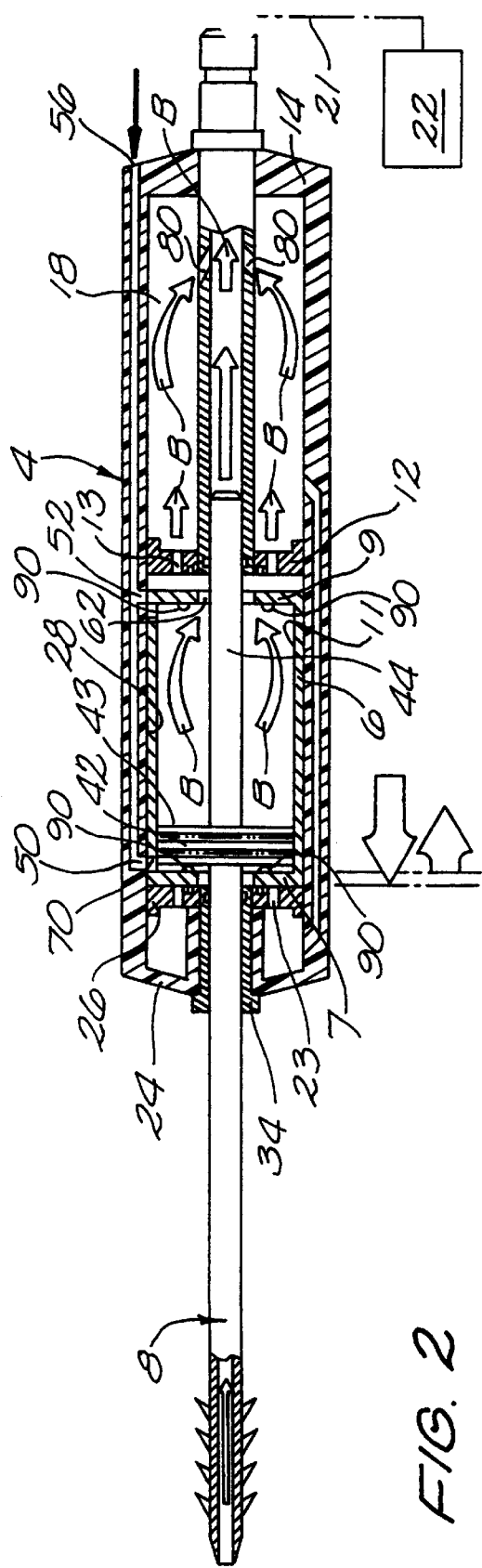
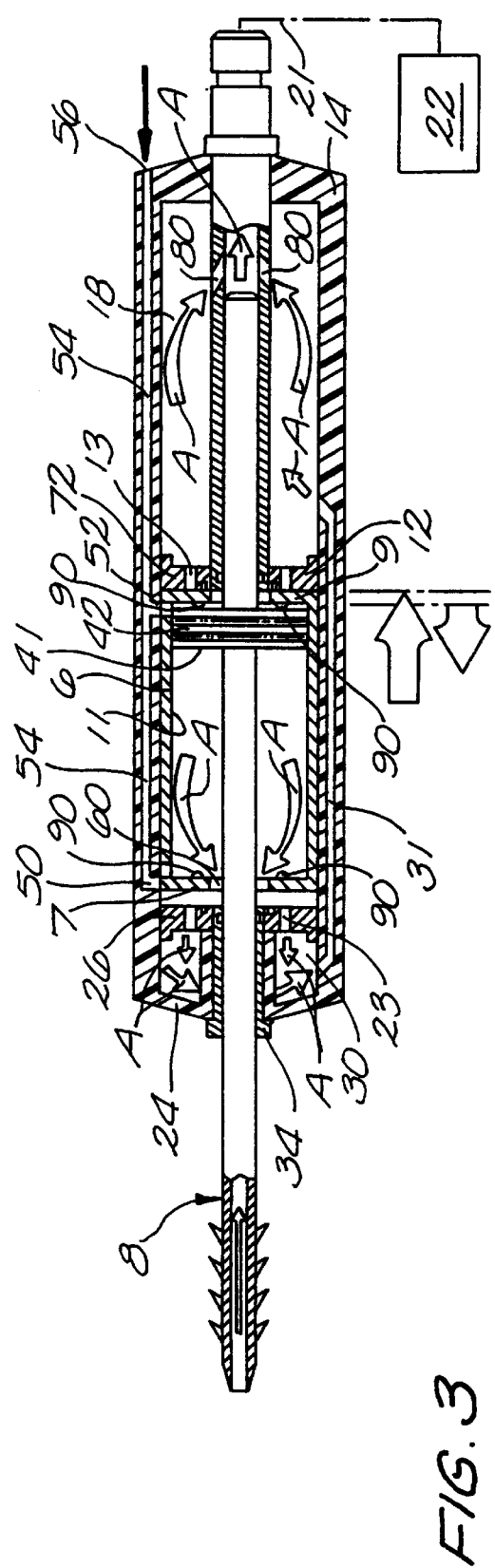
FIG. 2
FIG. 3

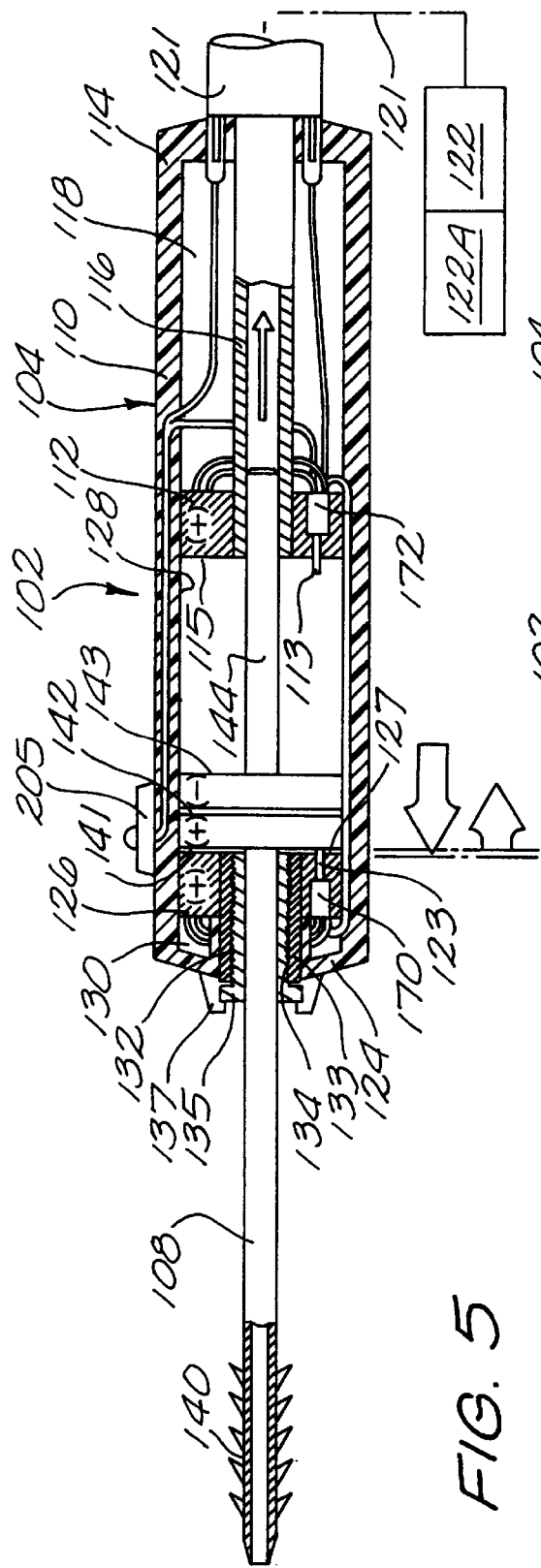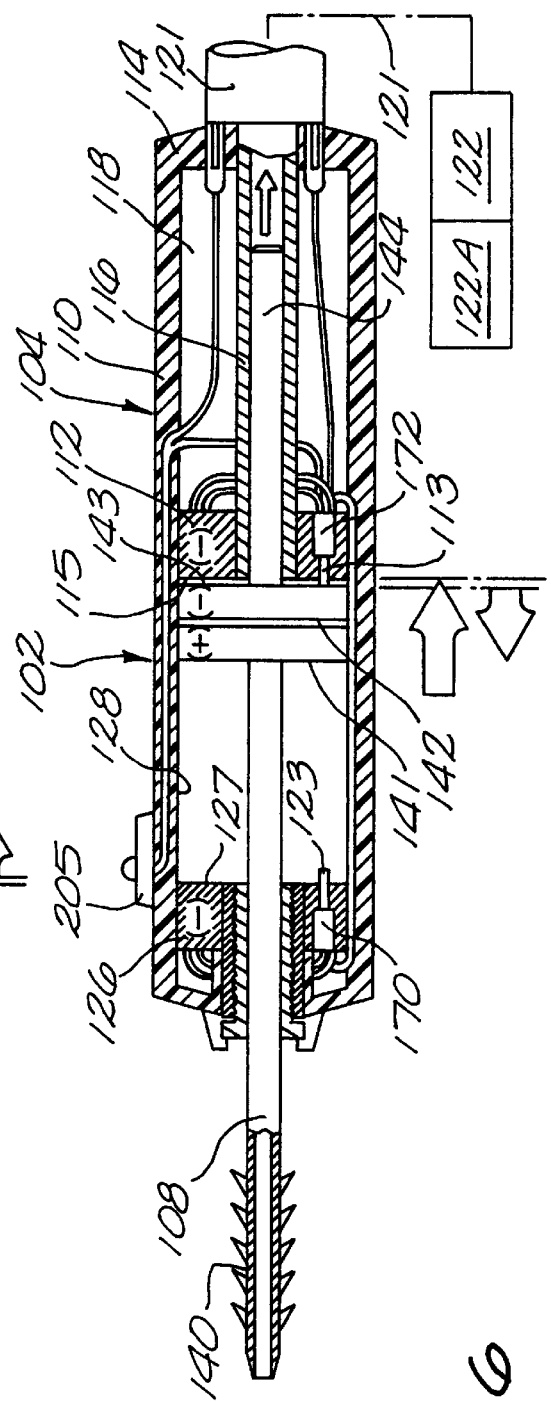
FIG. 5
FIG. 6

RECIPROCATING LIPOSUCTION DEVICE

TECHNICAL FIELD

This invention relates to a liposuction device having automatic reciprocal motion for the aspiration of fatty tissue without the need for the surgeon to manually perform back and forth movements of the cannula.

BACKGROUND ART

Liposuction is a surgical procedure performed to remove excess fatty tissue from the human body. The procedure is performed by inserting a suction cannula attached to a vacuum pump by means of tubing, into the fatty tissue. Back and forth movements of the cannula are then made by the surgeon in order to evenly remove the fat. Originally, reciprocation of the cannula was only performed manually by the surgeon. Now, there have been liposuction devices invented which provide for automatic reciprocation of the cannula. Some patents covering this automatic movement include U.S. Pat. Nos. 5,112,302; 5,352,194; and 5,348,535.

DISCLOSURE OF INVENTION

An object of the present invention is to provide a liposuction device having automatic reciprocal motion of a cannula. The motion can be created by the suction, or vacuum, created within the suction cannula, or electromagnetically by an arrangement of electromagnets and magnets of fixed polarity. There is thus no need for an additional power source using pressurized air or an electric motor to create the reciprocal motion.

Another object of this invention is to have a narrow handle that is easily and comfortably grassed by the surgeon's hand. Therefore, all additional parts should be housed within the handle, with only a vacuum device attachment to the handle.

A further object of this invention is to have two main chambers aligned in the handle, a rearward annular chamber and a forward cylindrical chamber, with a partition therebetween. A cylinder is mounted in said forward cylindrical chamber for reciprocal movement therein, and a suction tube forms the rearward annular chamber. A cannula is formed of a long tube with a piston fixed thereto which is mounted in said cylinder to move said cannula back and forth. The forward part of the cannula extends forwardly out of the handle and the suction tube extends rearwardly out of the handle. The rearward part of the cannula extends rearwardly into the suction tube.

Another object of the present invention is to provide an automatic reciprocating cannula where the reciprocation is powered by the negative pressure created by the suction being applied to the cannula.

A further object of the present invention is to provide an automatic reciprocating cannula where the reciprocation is powered by an electromagnetic device.

A further object of this invention is to provide for automatic reciprocal motion of a liposuction device electromagnetically, electrical power being supplied by means of wires in the suction tubing so that there is only one tubular connection or attachment to the cannula.

Another object of this invention is to provide an automatic movement which does not include vibration or rotation of a cannula, rotation being dangerous as nerves or blood vessels can be rolled up on the cannula.

A further object of this invention is to have two main chambers aligned in the handle, a rearward annular chamber and a forward cylindrical chamber, with a first electromagnetic device forming a partition therebetween. A second electromagnetic device forms the front wall of the forward cylindrical chamber. A suction tube forms the rearward annular chamber. A cannula is formed of a long tube with a piston fixed thereon formed as a permanent magnet, which piston is mounted in said forward cylindrical chamber to move the cannula back and forth. The forward part of the cannula extends forwardly out of the housing and the suction tube extends rearwardly out of the housing. The rearward part of the cannula extends rearwardly through the first electromagnetic device into the suction tube.

Another object of this invention is to have spaced electromagnetic devices which will provide reciprocation of a cannula having a permanent magnetic device thereon.

Another object of this invention is to provide a suction tubing with the wires for the electromagnetic devices being embedded along the length of the tubing so there will be no interference with the surgeon's control of the operation.

BRIEF DESCRIPTION OF THE DRAWINGS

FIG. 2 is a view similar to FIG. 1 where the control cylinder has reached its forward position and the cannula piston now has a negative pressure placed on the rearward face of the cannula piston to move the cannula rearwardly;

FIG. 3 is a view similar to FIG. 1 where the control cylinder has reached its rearward position and the cannula piston now has a negative pressure placed on the forward face of the cannula piston to move the cannula forwardly, as in FIG. 1.

FIG. 5 is a view similar to FIG. 4 where the magnetic piston has reached its forward position and the forward switch device has been activated to reverse the polarity of both electromagnetic devices, thereby reversing the electromagnetic force acting on the magnetic piston and the cannula will be moved rearwardly; and FIG. 6 is a view similar to FIG. 4 where the magnetic piston has reached its rearward position and the rearward switch device has been activated to reverse the polarity of both electromagnetic devices, thereby reversing the electromagnetic force acting on the magnetic piston and the cannula will be moved forwardly, as in FIG. 1.

BEST MODE FOR CARRYING OUT THE INVENTION

Figure 1:
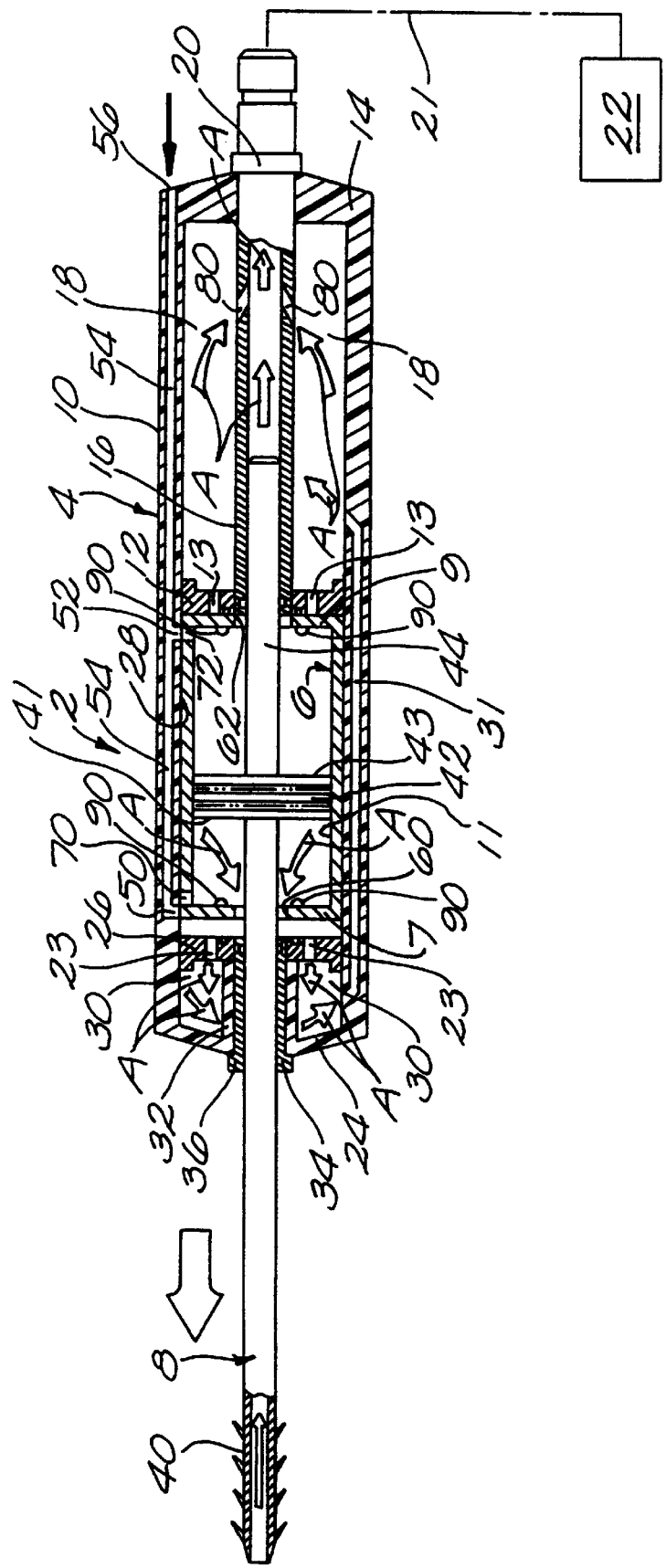
FIG. 1 is a longitudinal sectional view of a reciprocating liposuction device with its cannula connected to a vacuum source and the control cylinder being positioned to place a negative pressure on the forward face of a cannula piston to move the cannula forwardly.

The liposuction device 2 of FIG. 1 comprises three (3) main parts:

(1) an elongated housing 4 which is formed to be handheld by an operator;

(2) a reciprocable hollow cylinder 6 in said housing;

(3) a reciprocable cannula 8 being slideably mounted in said housing 4 and having a piston 42 fixed thereon slideably mounted in said hollow cylinder 6.

The housing 4 is formed as an elongated cylinder 10 having a fixed partition 12 at a mid-portion thereof. The rear end of the elongated cylinder 10 is closed by an end wall 14. The fixed partition 12 and the end wall 14 each have an aligned opening therein at the center thereof to receive a suction tube 16 fixed therein. This arrangement forms an annular fixed chamber 18 in the rear end of the elongated cylinder 10. The suction tube 16 has a short section extending externally of the rear end wall 14. A flange 20 on the suction tube 16 abuts the outer side of the rear end wall 14. The exterior end of the suction tube 16 is formed to receive the end of a flexible tube 21 from a vacuum device 22. The interior end of the suction tube 16 ends at the forward side of the mid-portion fixed partition 12.

The forward end of the elongated cylinder 10 is closed by an end wall 24. A forward fixed partition 26 is positioned to form a fixed cylindrical chamber 28 with mid-portion fixed partition 12, approximately the same length as annular fixed chamber 18, and a small annular chamber 30 with forward end wall 24. A short tubular member 32 connects an opening at the center of the forward fixed partition 26 with an opening at the center of the forward end wall 24. A cylindrical bearing member 34 is fixedly mounted in the short tubular member 32, which has the same diameter as suction tube 16, for a purpose to be hereinafter described.

A flange 36 on the cylindrical bearing member 34 abuts the outer side of the forward end wall 24. The interior end of the cylindrical bearing member 34 ends at the rearward side of the forward fixed partition 26.

The cylinder 6, having a forward end wall 7 and rearward end wall 9 with a cylindrical bore 11 therebetween, is slideably mounted in fixed cylindrical chamber 28 for a short distance for a purpose to be hereinafter described. The cannula 8 has a forward tubular end 40 for penetrating a human body to remove excess fatty tissue, a fixed piston 42 for slideable reciprocal movement in the cylindrical bore 11 of cylinder 6, and a rearward tubular end 44 for directing fatty tissue to said suction tube 16.

Annular chamber 18 is connected to the rearward end of cylindrical chamber 28 by openings 13, and small annular chamber 30 is connected to the forward end of cylindrical chamber 28 by openings 23. The small annular chamber 30 is connected to the annular chamber 18 by a longitudinal passage 31.

The forward end 40 of the cannula 8 extends from the forward center of the piston 42 through an enlarged opening 60 in the forward wall of the cylinder 6 and is slideably mounted in the cylindrical bearing member 34 for reciprocal movement. The rearward end 44 of the cannula 8 extends from the rearward center of the piston 42 through an enlarged opening 62 in the rearward wall of the cylinder 6 and is slideably mounted in the suction tube 16.

The fixed cylindrical chamber 28 is connected at its forward end by an opening 50, and at its rearward end by an opening 52, to a longitudinal vent passage 54 located in the wall of the housing 4. The end 56 of the vent passage 54 is open to the atmosphere.

Cylinder 6 has an opening 70 for alignment with opening 50 when the cylinder 6 has been moved to its forward position in fixed cylindrical chamber 28, and cylinder 6 has an opening 72 for alignment with opening 52 when the cylinder 6 has been moved to its rearward position in fixed cylindrical chamber 28 to permit proper control flow. Openings 80 connect the annular chamber 18 to the rearward part of suction tube 16 in the chamber 18. Projections 90 on the inner faces of the forward end wall 7 and rearward end wall 9 of cylinder 6 provide for a space when engaged by the piston 42 so that venting is assured.

Operation

With the liposuction device 2 as shown in FIG. 1 with the vacuum source 22 on, a negative pressure is placed on the end of suction tube 16 and extends through the cannula 8. Further, a negative pressure is placed through openings 80 into annular chamber 18, where it is placed in small annular chamber 30 through longitudinal passage 31. The negative pressure passes through openings 23, the space between the rearward side of the forward fixed partition 26 and forward side of the forward end wall 7 of cylinder 6, and enlarged opening 60 to place the negative pressure on the forward face 41 of piston 42 to draw it forwardly. The piston 42 will move forward in cylindrical bore 11 until it reaches the position shown in FIG. 2 where it forces the forward end wall 7 of cylinder 6 against the rearward side of the forward fixed partition 26, closing openings 23 and pulls the rearward end wall 9 of cylinder 6 away from the forward side of the mid-portion fixed partition 12, opening the openings 13 wherein the negative pressure in annular chamber 18 will be delivered to the rearward face 43 of piston 42 to draw it rearwardly. In FIGS. 1 and 3, negative pressure is indicated be arrows A.

With the liposuction device 2, as shown in FIG. 2 with the vacuum source 22 on, the negative pressure in annular chamber 18 now is placed through openings 13, the space between the forward side of the mid-portion fixed partition 12 and rearward side of the rearward end wall 9 of cylinder 6, and enlarged opening 62 to place the negative pressure on the rearward face 43 of piston 42 to draw it rearwardly. The piston 42 will move rearward in cylinder bore 11 until it reaches the position shown in FIG. 3 where it forces the rearward end wall 9 of cylinder 6 against the forward side of the mid-portion fixed partition 12, closing the openings 13 and pulls the forward end wall 7 of cylinder 6 away from the rearward side of the forward fixed partition 26, opening the openings 23 wherein the negative pressure in annular chamber 18 will be delivered to the forward face 41 of piston 42 to draw it forward. In FIG. 2, negative pressure is indicated by arrows B.

FIG. 3 shows the reversing of the reciprocating movement to return to the movement as shown in FIG. 1.

Figures 4, 4A:
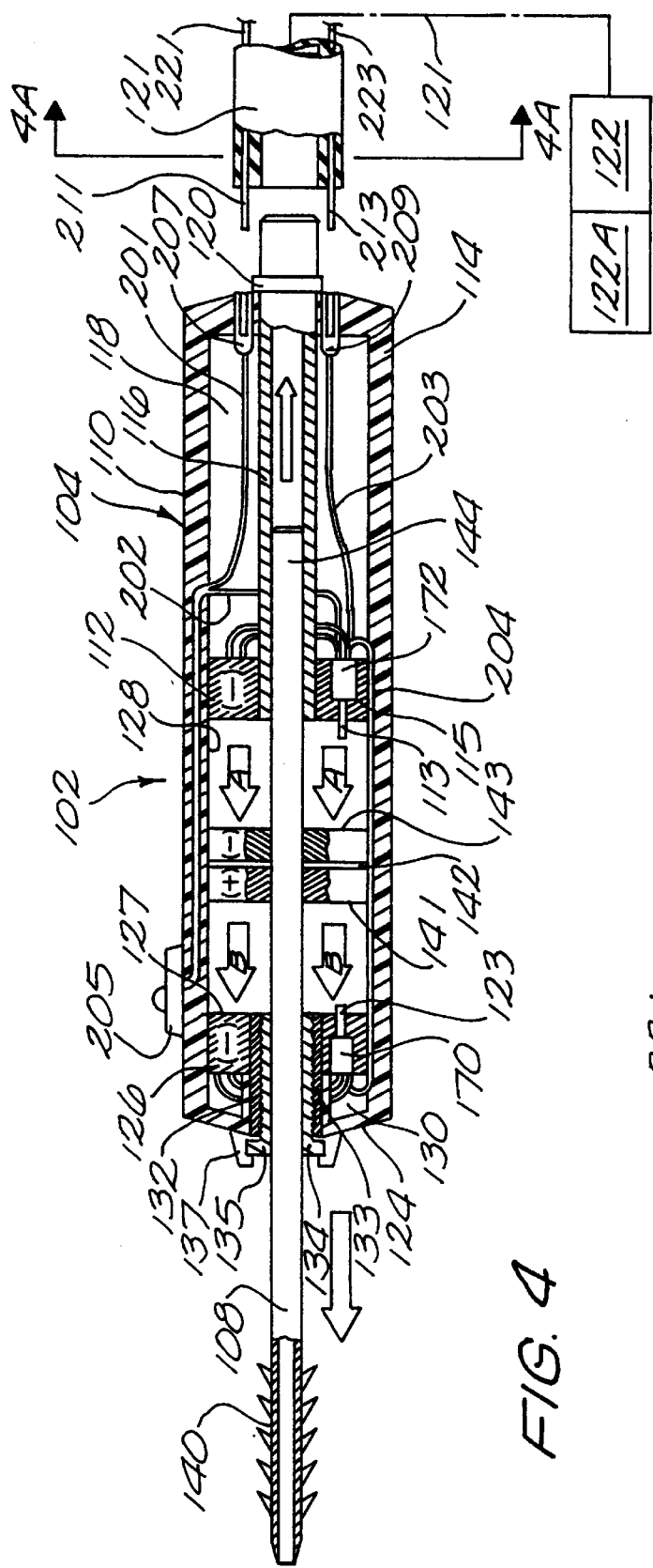
FIG. 4 is a longitudinal sectional view of another modification of a reciprocating liposuction device with its cannula connected to a vacuum source with a cannula piston on the cannula being formed as a magnetic device having a fixed positive polarity on one face and a fixed negative polarity on the other face, with electromagnetic devices on each side of the magnetic device activated to move the cannula forwardly.
FIG. 4a is a view taken on the line 4a—4a showing the construction of the flexible tube connected to the liposuction device containing the electric wires for the electromagnets.

The liposuction device 102 of FIG. 4 comprises four (4) main parts:

(1) an elongated housing 104 which is formed to be hand-held by an operator;

(2) an electromagnet forms a mid-portion fixed partition 112;

(3) an electromagnet forms a forward movable partition 126; the electromagnetic partitions 112 and 126 form a cylindrical chamber 128;

(4) a reciprocable cannula 108 is slideably mounted in said housing 104 and has a magnetized piston 142 fixed thereon for slideable movement in cylindrical chamber 128.

The housing 104 is formed as an elongated cylinder 110 having a fixed electromagnetic partition 112 at a mid portion thereof. The rear end of the elongated cylinder 110 is closed by an end wall 114. The fixed partition 112 and the end wall 114 each have an aligned opening therein at the center thereof to receive a suction tube 116 fixed therein. This arrangement forms an annular fixed chamber 118 in the rear end of the elongated cylinder 110. The suction tube 116 has a short section extending externally of the rear end wall 114. A flange 120 on the suction tube 116 abuts the outer side of the rear end wall 114. The exterior end of the suction tube 116 is formed to receive the end of a flexible tube 121 from a vacuum device 122. The flexible tube 121 has wires embedded along the length of the tubing to provide electricity to the electromagnets 112 and 126 by prongs 211 and 213 extending from the end. This arrangement will be hereinafter described. The electrical source is located shown with the vacuum device 122. The interior end of the suction tube 116 ends at the forward side of the mid-portion electromagnetic fixed partition 112.

The forward end of the elongated cylinder 110 is closed by an end wall 124. The forward movable partition 126 is positioned in the elongated cylinder 110 to form a cylindrical chamber 128, variable in length, with mid-portion fixed partition 112. This forward movable partition 126 also forms a small annular chamber 130 with forward end wall 124.

A short tubular member 132 extends rearwardly from an opening at the center of the forward end wall 124 and provides a forward stop for the movable partition 126. Movable partition 126 has an internally threaded sleeve 133 fixed thereto extending therethrough from the rearward face of the movable partition 126 and to the forward end of the forward end wall 124 when the partition 126 is against the rear end of the short tubular member 132. In the forward position of the movable partition 126, an externally threaded bearing and adjustment member 134 is threaded into the internally threaded sleeve 133 and has a flanged head 135 which abuts the forward face of the forward end wall 124 and reaches to the rearward face of the movable partition 126. Holding members 137 prevent axial movement of the bearing and adjustment member 134 so that rotation of the bearing and adjustment member 134 will axially move the movable partition 126 to vary the length of the cylindrical chamber 128, if desired, to control the length of movement of the reciprocable cannula 108 of the liposuction device 102. The bearing and adjustment member 134 provides a cylindrical bearing surface for a purpose to be hereinafter described.

The forward end 140 of the cannula 108 extends from the forward center of a piston 142 through the cylindrical bearing surface of the bearing and adjustment member 135 and is slideably mounted therein for reciprocal movement. The rearward end 144 of the cannula 108 extends from the rearward center of the piston 142 and extends into the suction tube 116 where it is mounted for slideable movement.

The cannula piston 142 is permanently magnetized so that it will be positive (+) on the face and negative (−) on the other face. As seen in FIG. 4, the magnetized piston 142 is arranged so that the rearward face 143 is negative (−) and the forward face 141 is positive (+). The reciprocal cannula 108 is permitted movement in cylindrical chamber 128 between the rearward face 127 of the forward electromagnetic movable partition 126 and the forward face 115 of the mid-portion electromagnetic fixed partition 112 by engagement with the cooperating forward positive (+) face 141 of the magnetized piston 142 and the rearward negative (−) face 143 of the magnetized piston 142.

The forward movable electromagnetic partition 112 has an electric switching device 170 located therein with an actuating pin 123 projecting into the chamber 128 through its rearward face 127. The switching device 170 has an electrical connection to both electromagnetic partitions 112 and 126 to simultaneously change the charge on the forward face 115 of electromagnetic partition 112 and the rearward face 127 of electromagnetic partition 126 when the actuating pin 123 is actuated by engagement with the positive (+) forward face 141 of the permanently magnetized piston 142 in the forward position of the cannula 108. Note FIG. 5 where the forward face 141 of magnetized piston 142 has reached its forward position and actuated the switching device 170 changing the charge on the rearward face 127 of electromagnetic partition 126 to a positive charge (+) and the charge on the forward face 115 of electromagnetic partition 112 to a positive charge (+).

The mid-portion fixed electromagnetic partition 112 has an electric switching device 172 located therein with an actuating pin 113 projecting into the chamber 128 through its forward face 115. The switching device 172 has an electrical connection to both electromagnetic partitions 112 and 126 to simultaneously change the charge on the forward face 115 of electromagnetic partition 112 and the rearward face 127 of electromagnetic partition 126 when the actuating pin 113 is actuated by engagement with the negative (−) rearward face 143 of the permanently magnetized piston 142 in the rearward position of the cannula 108. Note FIG. 6 where the rearward face 143 of magnetized piston 142 has reached its rearward position and actuated the switching device 172, changing the charge on the rearward face 127 of electromagnetic partition 126 to a negative charge (−) and the charge on the forward face 115 of electromagnetic partition 112 to a negative charge (−).

Electricity is directed to the electric switching devices 170 and 172 by conduits 201, 202, 203, and 204. A manually operated "ON-OFF" switch 205 is positioned on the housing 104 between the conduits 201 and 202, to turn the liposuction device 102 "on" or "off". Conduits 201 and 202 each have a single socket 207 and 209 positioned in end wall 114, respectively, to receive electrical prongs 211 and 213. The prongs 211 and 213 extend from the end of the flexible tube 121 and are connected to an electrical source 122A, located with the vacuum device 122, by wires 221 and 223, respectively, in the wall of the flexible tube 121. This reduces the number of individual connections to the liposuction device. A plurality of connections may hinder the accurate control which the surgeon needs to maintain during operation.

Operation

With the liposuction device 102 as shown in FIG. 4, with the "ON-OFF" switch 205 in its "on" position, the forward face 115 of electromagnetic partition 112 has a negative charge (−) and the rearward face 127 of electromagnetic partition 126 also has a negative charge (−). It can be seen that the negative (−) rearward face 143 of the permanently magnetized piston 142 is repelled by the negatively charged (−) forward face 115 of electromagnetic partition 112, and the positive (+) forward face 141 of the permanently magnetized piston 142 is attracted to and drawn toward the negatively charged (−) rearward face 127 of electromagnetic partition 126. The repelling action between electromagnetic partition 112 and permanently magnetized piston 142 is shown by arrows A and the attracting action between the permanently magnetized piston 142 and the electromagnetic partition 126. It can be seen that with this arrangement the cannula 108 is moved in a forward direction.

When the permanently magnetized piston 142 reaches its forwardmost position, as shown in FIG. 5, the switching device 120 is actuated by the movement of the actuating pin 123 by engagement with piston 142. This actuation reverses the charge on the rearward face 127 of electromagnetic partition 126 and the charge on the forward face 115 of electromagnetic partition 112 from a negative charge (−) to a positive charge (+). Now, the rearward face 127 of electromagnetic partition 126 with a positive charge (+) will repel the positive (+) forward face 141 of the permanently magnetized piston 142, and the forward face 115 of electromagnetic partition 112 with a positive charge (+) will attract the negative (−) rearward face 143 of the permanently magnetized piston 142. It can be seen that with this arrangement the cannula 108 is moved in a rearward direction.

When the permanently magnetized piston 142 reaches its rearwardmost position, as shown in FIG. 6, the switching device 172 is actuated by the movement of the actuating pin 113 by engagement with piston 142. This actuation reverses the charge on the forward face 115 of electromagnetic partition 112 and the charge on the rearward face 127 of electromagnetic partition 126 from a positive charge (+) to a negative charge (−). Now, as shown in FIG. 4, the forward face 115 of electromagnetic partition 112 with a negative charge (−) repels the negative (−) rearward face 143 of the permanently magnetized piston 142, and the positive (+) forward face 141 of the permanently magnetized piston 142 is attracted to the negatively charge (−) rearward face 127 of electromagnetic partition 126. The cannula 108 will now move in a forward direction.

While the "ON-OFF" switch 205 is turned "on", the back and forth movement of the cannula 108 will continue.

While the principles of the invention have now been made clear in an illustrative embodiment, it will become obvious to those skilled in the art that many modifications in arrangement are possible without departing from those principles. The appended claims are, therefore, intended to cover and embrace any such modifications, within the limits of the true spirit and scope of the invention.

I claim:

1. A reciprocating liposuction device comprising:
   (a) a hand holdable housing with a forward end and a rearward end, said housing having a cylindrical chamber;
   (b) a single rigid tubular cannula having a forward end and a rearward end, the forward end of said tubular cannula extending through said forward end of said housing, said tubular cannula further having a piston fixedly mounted thereon;
   (c) means for mounting said piston in the forward cylindrical chamber;
   (d) a suction tube extending through the rearward end of said housing and the rearward end of said tubular cannula slideably attached to a forward end of said suction tube; and,
   (e) means for providing reciprocal movement of said piston within said cylindrical chamber.

2. The reciprocating liposuction device according to claim 1 further including:
   (a) means for creating a suction force within said suction tube; and,
   (b) means for selectively communicating the suction force from said means for creating a suction force to alternating ends of the cylindrical chamber.

3. The reciprocating liposuction device as set forth in claim 2 further including means for selectively applying air pressure to alternating ends of the cylindrical chamber, said means for selectively applying air pressure being out of phase with said means for selectively communicating the suction force.

4. The reciprocating liposuction device according to claim 1 wherein the piston includes a permanent magnet and further including:
   (a) a first and a second electro-magnet positioned on opposing ends of said cylindrical chamber; and,
   (b) switching means for alternating electromagnetic poles between said first and second electro-magnets.

5. The reciprocating liposuction device according to claim 4 further including an actuation pin extending into the forward cylindrical chamber and wherein said switching means is activated by said actuation pin.

6. The reciprocating liposuction device according to claim 1 wherein a forward end of said tubular cannula is adapted for removal of fatty tissue from a patient.

7. A medical aspiration apparatus comprising:
   (a) means for providing suction;
   (b) a hand-held surgical instrument having,
      (1) a forward end,
      (2) an enclosed chamber,
      (3) a cannula having a forward end and a rearward end, the forward end of said cannula extending through said forward end of said hand-held surgical instrument, a shaft portion of said cannula proximate to the forward end thereof adapted to easily reciprocate while in contact with a patient's tissue, said cannula further having a piston fixedly mounted thereon and adapted to lie with said chamber, and,
      (4) means for providing reciprocal movement of said piston within said chamber; and,
   (c) a suction tube communicating with the rearward end of said cannula with said means for providing suction such that the rearward end of said cannula slideable moveable within said suction tube.

8. The medical aspiration apparatus according to claim 7 further including means for pneumatically driving said piston within said enclosed chamber.

9. The medical aspiration as set forth in claim 8 further including means for selectively applying air pressure to alternating ends of said enclosed chamber.

10. The medical aspiration apparatus according to claim 7 wherein the piston includes a permanent magnet and further including:
    (a) a first and a second electro-magnet positioned on opposing ends of said enclosed chamber; and,
    (b) switching means for alternating electromagnetic poles between said first and second electro-magnets.

11. The medical aspiration apparatus according to claim 10 further including an actuation pin extending into the forward cylindrical chamber and wherein said switching means is activated by said actuation pin.

12. The medical aspiration apparatus according to claim 7 wherein a forward end of said cannula is adapted for removal of fatty tissue from a patient.

* * * * *